US009206461B2

(12) United States Patent
Tokonami et al.

(10) Patent No.: US 9,206,461 B2
(45) Date of Patent: Dec. 8, 2015

(54) MICROORGANISM DETECTION SENSOR AND METHOD OF MANUFACTURING THE SAME

(75) Inventors: Shiho Tokonami, Sakai (JP); Hiroshi Shiigi, Sakai (JP); Tsutomu Nagaoka, Sakai (JP); Mugihei Ikemizu, Osaka (JP); Mari Takahashi, Osaka (JP)

(73) Assignees: OSAKA PREFECTURE UNIVERSITY PUBLIC CORPORATION, Osaka (JP); SHARP KABUSHIKI KAISHA, Osaka (JP)

( * ) Notice: Subject to any disclaimer, the term of this patent is extended or adjusted under 35 U.S.C. 154(b) by 0 days.

(21) Appl. No.: 14/003,613

(22) PCT Filed: Mar. 6, 2012

(86) PCT No.: PCT/JP2012/055611
§ 371 (c)(1),
(2), (4) Date: Sep. 6, 2013

(87) PCT Pub. No.: WO2012/121229
PCT Pub. Date: Sep. 13, 2012

(65) Prior Publication Data
US 2013/0337498 A1   Dec. 19, 2013

(30) Foreign Application Priority Data
Mar. 8, 2011   (JP) .................................. 2011-050416

(51) Int. Cl.
| | |
|---|---|
| *C12Q 1/04* | (2006.01) |
| *G01N 33/569* | (2006.01) |
| *G01N 33/543* | (2006.01) |
| *C25D 5/00* | (2006.01) |

(52) U.S. Cl.
CPC .. *C12Q 1/04* (2013.01); *C25D 5/00* (2013.01); *G01N 33/5438* (2013.01); *G01N 33/569* (2013.01); *Y10T 428/24479* (2015.01)

(58) Field of Classification Search
None
See application file for complete search history.

(56) References Cited

U.S. PATENT DOCUMENTS

| | | | | |
|---|---|---|---|---|
| 2004/0126814 A1* | 7/2004 | Singh et al. | ..................... | 435/7.1 |
| 2009/0012446 A1* | 1/2009 | Cui et al. | ......................... | 604/20 |
| 2012/0258444 A1* | 10/2012 | Therrien et al. | .................. | 435/5 |

FOREIGN PATENT DOCUMENTS

JP   2009-58232 A   3/2009

OTHER PUBLICATIONS

Beck, J.D., Shang, L., Li, B., Marcus, M.S., and Hamers, R.J. "Discrimination between Bacillus Species by Impedance Analysis of Individual Dielectrophoretically Positioned Spores", Analytical Chemistry 2008, vol. 80, pp. 3757-3761.*
Dickert, F.L., Lieberzeit, P.A., and Hayden, O. "Molecularly Imprinted Polymers for Mass Sensitive Sensors—from Cells to Viruses and Enzymes", Molecular Imprinting of Polymers, Chapter 8; Eurekah/Landes Bioscience: Georgetown, Texas, 2004; pp. 9-10.*
International Search Report issued in PCT/JP2012/055611 mailed Apr. 24, 2012.
Cohen et al., "Whole Cell Imprinting in Sol-Gel Thin Films for Bacterial Recognition in Liquids:Macromolecular Fingerprinting", Int. J. Mol. Sci., vol. 11, No. 4, 2010, pp. 1236-1252.
Dickert et al., "Bioimprinted QCM sensors for virus detection-screening of plant sap", Anal Bioanal Chem, vol. 378, No. 8, 2004, pp. 1929-1934.
Harvey et al., "Preparation and evaluation of spore-specific affinity-augmented bio-imprinted beads", Anal Bioanal Chem, vol. 386, No. 2, 2006, pp. 211-219.
Takeda et al., "A Highly Sensitive Amperometric Adenosine Triphosphate Sensor Based on Molecularly Imprinted Overoxidized Polypyrrole", J. Flow Injection Anal., vol. 25, No. 1, 2008, pp. 77-79.
Nakadoi, Yu et al., "Development of virus sensor using molecularly imprinted overoxidized polypyrrole film," Extended Abstracts, Japan Society for Applied Physics and Related Societies, Mar. 9, 2011, vol. 58, p. 12-407.

* cited by examiner

*Primary Examiner* — Renee Claytor
*Assistant Examiner* — Michelle F Paguio Frising
(74) *Attorney, Agent, or Firm* — Birch Stewart Kolasch & Birch, LLP

(57) ABSTRACT

The present invention provides a sensor including a detection unit having a detection electrode and a polymer layer that is disposed on the detection electrode and includes a mold having a three-dimensional structure complementary to a steric structure of a microorganism to be detected. The sensor detects the microorganism based on a state of capturing the microorganism in the mold. The polymer layer is formed by a manufacturing method including: a polymerization step of polymerizing a monomer in the presence of the microorganism to be detected, to form the polymer layer having captured the microorganism on the detection electrode; a destruction step of partially destroying the microorganism captured in the polymer layer; and a peroxidation step of peroxidizing the polymer layer to release the microorganism from the polymer layer.

12 Claims, 14 Drawing Sheets

PSEUDOMONAS AERUGINOSA
(Pseudomonas aeruginosa)
ZETA POTENTIAL : −33.87 mV

ACINETOBACTER CALCOACETICUS
(Acinetobacter calcoaceticus)
ZETA POTENTIAL : −28.14 mV

POLYMERIZATION STEP IN PRESENCE OF PSEUDOMONAS AERUGINOSA

LYSOZYME 30 MINUTES
Triton 20 MINUTES

LYSOZYME 60 MINUTES
Triton 40 MINUTES

LYSOZYME 90 MINUTES
Triton 60 MINUTES

PEROXIDATION STEP FOR PSEUDOMONAS AERUGINOSA MOLD

MICROORGANISM DETECTION USING PSEUDOMONAS AERUGINOSA MOLD

POLYMERIZATION STEP IN PRESENCE OF ACINETOBACTER CALCOACETICUS

PEROXIDATION STEP FOR ACINETOBACTER CALCOACETICUS MOLD

MICROORGANISM DETECTION USING ACINETOBACTER CALCOACETICUS MOLD

MICROORGANISM DETECTION USING ESCHERICHIA COLI MOLD

MICROORGANISM DETECTION USING PSEUDOMONAS AERUGINOSA MOLD

MICROORGANISM DETECTION USING FOUR TYPES OF MOLDS

MICROORGANISM DETECTION USING FOUR TYPES OF MOLDS

MICROORGANISM DETECTION USING FOUR TYPES OF MOLDS

MICROORGANISM DETECTION USING FOUR TYPES OF MOLDS

MICROORGANISM DETECTION SENSOR AND METHOD OF MANUFACTURING THE SAME

TECHNICAL FIELD

The present invention relates to a sensor for detecting microorganisms, and a method of manufacturing the sensor.

BACKGROUND ART

In recent years, there has been increasing interest in microorganism detection in medical industry, food industry, agriculture industry, livestock industry, aquaculture industry, a water-treatment facility, and the like. Only small amounts of contaminating microorganisms existing in food, drugs, agricultural chemicals and the like can exert a significant influence on human health. Also, microorganism contamination in hospitals and senior care facilities has been recognized as a social problem. Furthermore, there has been increasing interest also in hygiene management in ordinary households as can be seen from the fact that various of antibacterial goods are distributed in the market and the demand for such goods are growing. For example, in food-processing plants, a bacteria test is performed by sampling the food to be shipped, and also performed in the environment within the plants. In this case, however, when measurements are made by a culture method, it takes about 24 to 48 hours to obtain results, which may cause an increase in the storage cost until the food is shipped. Therefore, a quick detection method is demanded. Also in the agricultural sector, for example, when the bacterial number in the culture solution for hydroponic culture is increased, the risk of developing a disease is increased. If the bacterial number can be grasped as early as possible, measures such as sterilization can be taken immediately. Therefore, a quick detection method is effective.

Under such circumstances, recently, there is a rapidly growing need for a technique for allowing easy detection of microorganism contamination. Furthermore, it is necessary in medical practice to immediately identify a disease germ causing an infectious disease. Accordingly, there is also a need for a technique by which a disease germ can be detected quickly with high sensitivity. Examples of a method of detecting/identifying microorganisms may include the ELISA method, the western blotting method and the like. According to these methods, for example, after antibodies (primary antibody) and proteins specific to microorganisms are subjected to an antigen-antibody reaction, labeled secondary antibodies are caused to further react with the antibodies (primary antibody), to monitor the chemiluminescence of the secondary antibodies and the hydrolysis reaction of ATP, thereby accomplishing detection.

Furthermore, PTD 1 discloses a method of detecting a microbially-derived anion molecule (ATP, amino acid and the like) by utilizing the electrochemical properties of the polymer having a molecular mold.

CITATION LIST

Patent Document

PTD 1: Japanese Patent Laying-Open No. 2009-58232

SUMMARY OF INVENTION

Technical Problem

None of the above-described methods is, however, a method of detecting a microorganism itself. Also in the ELISA method and the like, it is necessary to produce an antibody for proteins and the like specific to microorganisms, which cannot be easily done.

An object of the present invention is to provide a novel microorganism detection sensor capable of quickly and simply detecting microorganisms with high sensitivity, and a method of manufacturing the microorganism detection sensor.

Solution to Problem

The present invention provides a sensor comprising a detection unit including a detection electrode and a polymer layer that is disposed on the detection electrode and includes a mold having a three-dimensional structure complementary to a steric structure of a microorganism to be detected. The sensor detects the microorganism based on a state of capturing the microorganism in the mold. The polymer layer is formed by a manufacturing method including: a polymerization step of polymerizing a monomer in presence of the microorganism to be detected, to form the polymer layer having captured the microorganism on the detection electrode; a destruction step of partially destroying the microorganism captured in the polymer layer; and a peroxidation step of peroxidizing the polymer layer to release the microorganism from the polymer layer.

The preferable embodiment of the sensor further includes a counter electrode and applies an alternating-current (AC) voltage between the detection electrode of the detection unit and the counter electrode in a state where the detection unit and the counter electrode are in contact with a sample solution, to direct the microorganism in the sample solution toward the detection unit by dielectrophoresis. The time period of applying the AC voltage is not particularly limited as long as the microorganism in the sample solution is directed toward the detection unit.

The preferable embodiment of the sensor further includes a crystal oscillator having the detection electrode of the detection unit as one of electrodes, and measures a change in a mass of the polymer layer based on a change in a resonance frequency of the crystal oscillator to detect the state of capturing the microorganism.

In the sensor, the monomer is preferably selected from the group consisting of pyrrole, aniline, thiophene, and derivatives thereof.

In the sensor, a surface of the detection electrode on which the polymer layer is formed is preferably a roughened surface.

In the sensor, it is preferable that the microorganism has entire electric charge or electric charge on a surface thereof that is excessively negatively charged. For example, the microorganism is a bacterium. In this case, the destruction step includes a step of performing a bacteriolysis process. For example, the bacterium may be *Pseudomonas aeruginosa*, *Acinetobacter calcoaceticus* or *Escherichia coli*.

Furthermore, the present invention provides a method of manufacturing a sensor detecting a microorganism. The sensor includes a detection unit having a detection electrode and a polymer layer that is disposed on the detection electrode and includes a mold having a three-dimensional structure complementary to a steric structure of the microorganism. The method includes: a polymerization step of polymerizing a monomer in presence of the microorganism to be detected, to form the polymer layer having captured the microorganism on the detection electrode; a destruction step of partially destroying the microorganism captured in the polymer layer;

and a step of peroxidizing the polymer layer to release the microorganism from the polymer layer.

In the preferable embodiment of the manufacturing method, the sensor further includes a counter electrode, and the polymerization step includes a step of applying a voltage between the detection electrode and the counter electrode that are in contact with a solution of the monomer, to electropolymerize the monomer.

In the preferable embodiment of the manufacturing method, the peroxidizing step includes a step of applying a voltage between the detection electrode and the counter electrode that are in contact with a solution within a range from neutral to alkaline, to peroxidize the polymer layer.

The preferable embodiment of the manufacturing method includes a surface-roughening step of roughening a surface of the detection electrode on which the polymer layer is fowled.

Advantageous Effects of Invention

According to the sensor of the present invention, microorganisms can be detected quickly and simply with high sensitivity. Furthermore, the method of manufacturing a sensor according to the present invention provides a sensor capable of detecting microorganisms quickly and simply with high sensitivity.

DESCRIPTION OF EMBODIMENTS

The sensor according to the present invention includes a detection unit having a detection electrode and a polymer layer that is disposed on the detection electrode and includes a mold having a three-dimensional structure complementary to a steric structure of a microorganism. The sensor serves to detect the microorganism based on the state of capturing the microorganism in the mold.

The polymer layer of the sensor according to the present invention is formed by a manufacturing method including: a polymerization step of polymerizing a monomer in the presence of a microorganism to be detected (which will be hereinafter referred to as a "target microorganism") to form a polymer layer having captured the microorganism on the detection electrode; a destruction step of partially destroying the microorganism captured in the polymer layer; and a peroxidation step of peroxidizing the polymer layer to release the microorganism from the polymer layer.

The preferable embodiments of the present invention will be hereinafter described with reference to the drawings.

[Production of Polymer Layer in Sensor]

Figure 1:
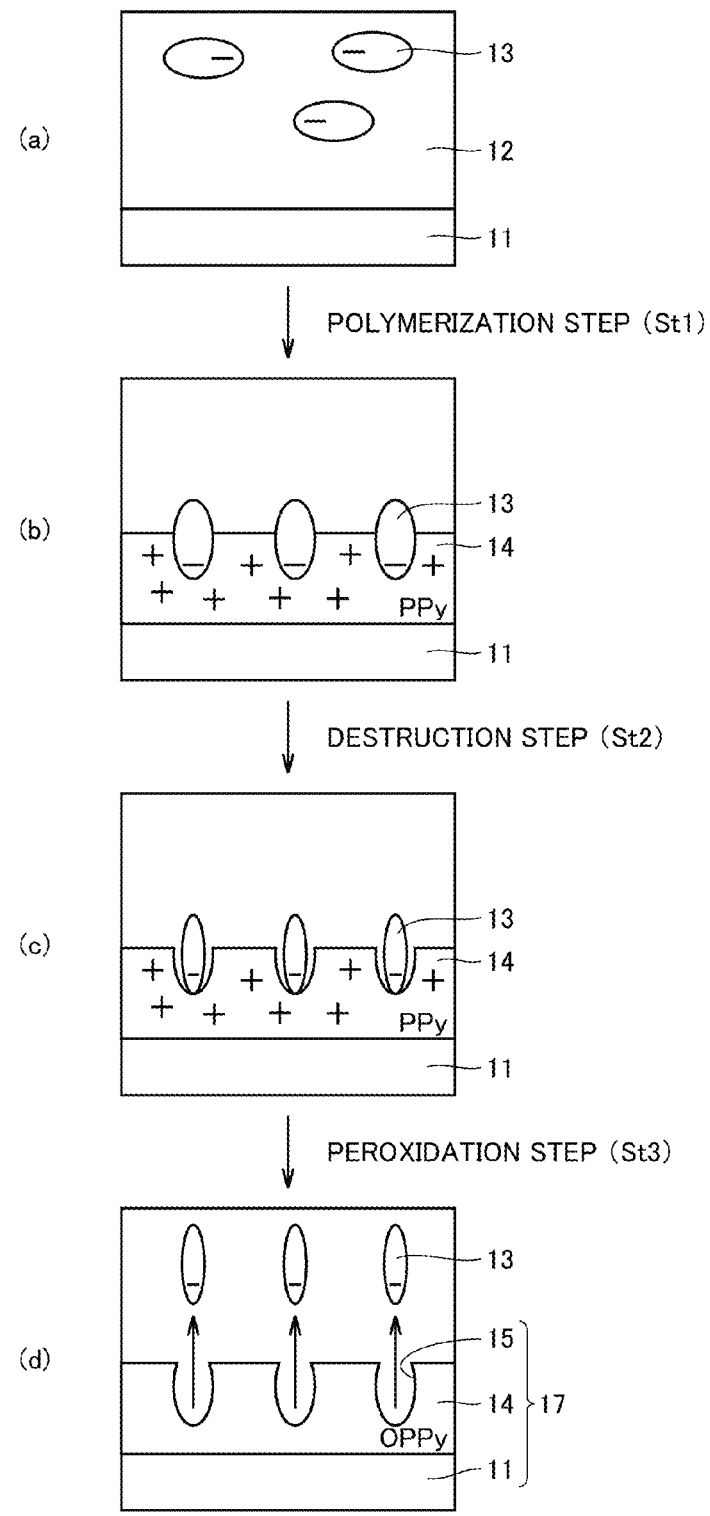
FIG. 1 schematically shows a preferable step of producing a polymer layer of a sensor according to the present invention, including cross-sectional views (a) before the polymerization step; (b) after the polymerization step; (c) after the destruction step; and (d) after the peroxidation step, respectively.

FIG. 1 is a cross-sectional view schematically showing a preferable step of producing a polymer layer of a sensor according to the present invention. FIG. 1 shows an embodiment in the case where pyrrole is used as a monomer. First, as shown in FIG. 1(a), a solution 12 containing microorganisms 13 and pyrrole is prepared under the environment where it is in contact with a detection electrode 11. In a polymerization step (St1), electrolysis is conducted using detection electrode 11 as an anode and a counter electrode (not shown) as a cathode. Then, by the oxidative polymerization reaction of pyrrole, a polymer layer 14 made of polypyrrole (which is abbreviated as "PPy" in FIG. 1(b)) is formed on detection electrode 11. Microorganisms 13 are captured in this formed polymer layer 14. Pyrrole itself contains a positive electric charge for emitting electrons to detection electrode 11 in the polymerization step. It is thus considered that, in order to make up for this positive electric charge, microorganism 13 having entire electric charge or electric charge on its surface that is excessively negatively charged is captured in polymer layer 14.

Then, in a destruction step (St2), as shown in FIG. 1(c), a destruction step of partially destroying microorganism 13 captured in polymer layer 14 is performed. The destruction step can be performed, for example, by addition of a degrading enzyme, temperature regulation, an ultrasonic treatment, an ozone treatment, existence of residual chlorine, and a bacteriophage process. When microorganism 13 is a bacterium, the destruction step can be performed by a bacteriolysis process using degrading enzymes such as lysozyme (the destruction step by the bacteriolysis process will be hereinafter also referred to as a "bacteriolysis step"). By this destruction step, the shape of microorganism 13 is changed, so that microorganism 13 is readily released from polymer layer 14.

Then, polymer layer 14 is peroxidized in a peroxidation step (St3). When polypyrrole forming polymer layer 14 is peroxidized, peroxidized polypyrrole (which is abbreviated as "Oppy" in FIG. 1(d)) is obtained, which is electrically neutral. Accordingly, microorganism 13 is released from polymer layer 14. The region of polymer layer 14 where microorganism 13 has existed is formed as a mold 15 having a three-dimensional structure complementary to the steric structure of microorganism 13. This peroxidation step (St3) also causes curing of polymer layer 14, thereby stabilizing mold 15 of microorganism 13. It is preferable that the peroxidation step (St3) is performed by adjusting solution 12 within a range from neutral to alkaline, and applying a voltage between detection electrode 11 and the counter electrode (not shown). A multilayer body of polymer layer 14 including mold 15 formed in this way and detection electrode 11 forms a detection unit 17 in the sensor according to the present invention.

The three-dimensional structure of the formed mold may be different depending on the solution composition in the peroxidation reaction and the voltage for triggering the peroxidation reaction. Generally, under such a condition that the peroxidation reaction gradually advances, a mold having a closely packed three-dimensional structure is formed by microorganism 13 to be detected.

Microorganism 13 to be detected is not particularly limited as long as it is a microorganism having entire electric charge or electric charge on its surface that is excessively negatively charged. Examples of microorganism 13 may be bacteria including the *Escherichia* group of *Escherichia coli*, the *Pseudomonas* group such as *Pseudomonas aeruginosa*, the *Acinetobacter* groups such as *Acinetobacter* calcoaceticus, and further, bacteria of the *Serratia* group, the *Klebsiella* group, the *Enterobacter* group, the *Citrobacter* group, the *Burkholderia* group, the *Sphingomonads* group, the *Chromobacterium* group, the *Salmonella* group, the *Vibrio* group, the *Legionella* group, the *Campylobacter* group, the *Yersinia* group, the *Proteus* group, the *Neisseria* group, the *Staphylococcus* group, the *Streptococcus* group, the *Enterococcus* group, the *Clostridium* group, the *Corynebacterium* group, the *Listeria* group, the *Bacillus* group, the *Mycobacterium* group, the *Chlamydia* group, the *Rickettsia* group, the *Haemophilus* group. Furthermore, examples of a virus may be a hepatitis A virus, an adenovirus, a rotavirus, and a norovirus. Examples of a fungus may be a *candida*. Examples of protozoa may be *Cryptosporidium*. Entire electric charge of the microorganism or electric charge on the surface thereof is changed by the water quality such as pH of solution 12. For example, there are various functional groups such as a carboxyl group, an amino group and a phosphate group on the surface of the microorganism. This surface on which these functional groups exist is negatively charged when pH is raised. Accordingly, in order to bring about an excessively negatively charged state when forming a mold or making measurements, solution 12 may be made alkaline, for example.

Although an explanation has been given in FIG. 1 with regard to the case where pyrrole is used as a monomer and a polypyrrole layer is formed as a polymer layer, the monomer used as a raw material of the polymer layer is not limited to pyrrole, but may be aniline, thiophene, derivatives thereof and the like.

The material of detection electrode 11 is not particularly limited, but may be a gold electrode, a multilayer electrode of gold and chromium, a multilayer electrode of gold and titanium, a silver electrode, a multilayer electrode of silver and chromium, a multilayer electrode of silver and titanium, a lead electrode, a platinum electrode, a carbon electrode, and the like. It is preferable that the surface of detection electrode 11 having polymer layer 14 formed thereon is subjected to a surface-roughening process. The surface of detection electrode 11 having polymer layer 14 formed thereon is a roughened surface, thereby providing effects of improving the adhesiveness to polymer layer 14 and expanding the surface area of the electrode. For example, when a gold electrode is used as detection electrode 11, the surface of the gold electrode is subjected to plasma etching, and then, gold nanoparticles are fixed thereto, thereby roughening this surface. In this way, the surface-roughening step can be performed.

[Capture of Target Microorganism in Mold]

Figure 2:
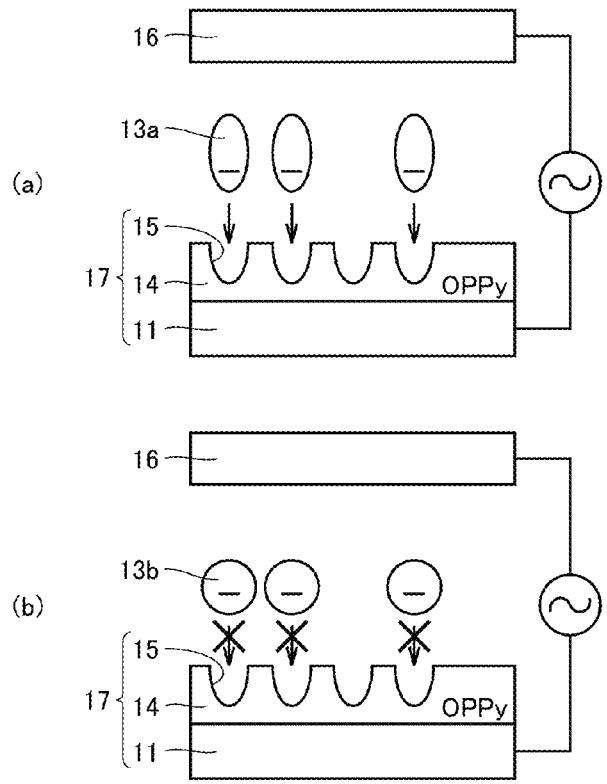
FIG. 2 is a diagram schematically showing the manner in which a target microorganism is captured in a mold in the sensor according to the present invention, including diagrams (a) in the case of the target microorganism and (b) in the case of not the target microorganism, respectively.

FIG. 2 is a diagram schematically showing the manner in which target microorganisms are captured in a mold. FIG. 2(a) shows the case where a microorganism 13a in a sample solution is a target microorganism, and FIG. 2(b) shows the case where a microorganism 13b in a sample solution is not a target microorganism. As shown in FIGS. 2(a) and 2(b), a sample solution is first prepared under the environment where this solution is in contact with detection unit 17 made of polymer layer 14 and detection electrode 11 and also contact with a counter electrode 16. Then, an AC voltage is applied between detection electrode 11 and counter electrode 16 to cause the microorganisms in the sample solution to be moved toward detection unit 17 by dielectrophoresis. In addition, counter electrode 16 is configured, the voltage to be applied is adjusted and the sample solution is prepared such that the microorganisms move toward detection electrode 11 by dielectrophoresis. When the microorganisms move toward detection electrode 11, microorganism 13a having a steric structure complementary to the three-dimensional structure of mold 15 is captured in mold 15 (FIG. 2(a)), but microorganism 13b that is not complementary to mold 15 is not captured in mold 15 (FIG. 2 (b)). Furthermore, even in the case where turbid materials such as mud and iron rust, for example, other than microorganisms are contained in water, these turbid materials are also different in three-dimensional shape, charged state and the like from mold 15 and not complementary to mold 15. Therefore, these turbid materials are not captured in mold 15. Consequently, a target microorganism can be distinguished from other turbid materials. Microorganisms can be separated from other turbid materials also by dielectrophoresis (dielectrophoresis can be performed on the conditions that microorganisms are collected in the electrode, but other turbid materials are not collected therein). In order to separate microorganisms from other turbid materials by dielectrophoresis, however, it is necessary to change the conditions for dielectrophoresis, such as frequency, in accordance with a change in the water quality such as electrical conductivity of water. In the case of the sensor according to the present invention, since a distinction can be made based on the shape of the object to be detected, the influence of the water quality is less likely to be exerted.

[Detection of Target Microorganism]

When microorganism 13a is captured in mold 15, the multilayer body made of polymer layer 14 and detection electrode 11 undergoes, for example, a mass change, a change in electrical conductive property, a change in electrical capacitance, a change in optical reflectance, a temperature change, and the like. The sensor according to the present invention detects the above-mentioned changes to detect the state of capturing microorganisms in mold 15. Thus, a target microorganism can be detected based on this capturing state. By detection as described above, the target microorganism can be quickly detected with high sensitivity. Specific examples of the method of detecting a mass change may be a method of detecting a change in the resonance frequency of the crystal oscillator. Hereinafter described will be a crystal oscillator microbalance (QCM) sensor, which is a preferable example of the sensor according to the present invention.

(QCM Sensor)

Figure 3:
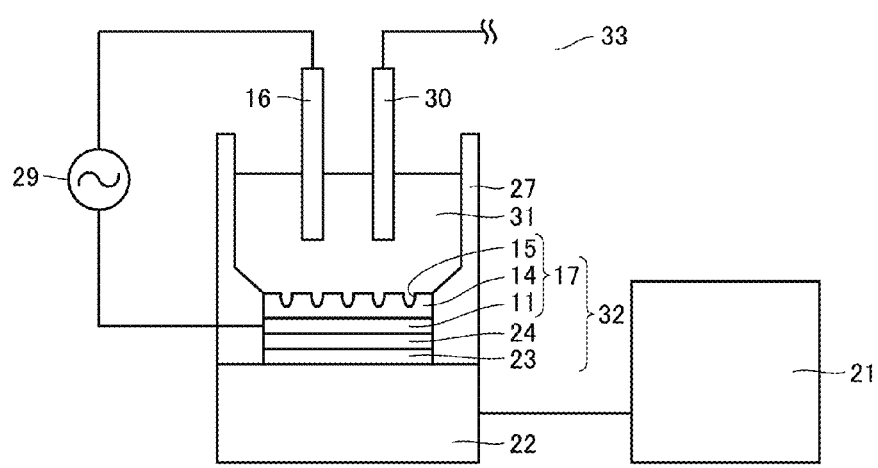
FIG. 3 is a diagram showing a schematic configuration of a QCM sensor according to the present invention.

FIG. 3 is a diagram showing the schematic configuration of a QCM sensor. A QCM sensor 33 includes a cell 27 storing a solution, a crystal oscillator 32 disposed at the bottom of cell 27, an oscillation circuit 22, and a controller 21 having a frequency counter. Crystal oscillator 32 is formed by stacking detection unit 17 produced by the steps shown in FIG. 1, a crystal piece 24, and a counter electrode (second counter electrode) 23 in this order. QCM sensor 33 further includes a counter electrode (first counter electrode) 16 and a reference electrode 30 immersed in a sample solution 31, and also includes an AC power supply 29 connected to detection electrode 11 of detection unit 17 and counter electrode 16.

First, sample solution 31 is added to cell 27. Then, AC power supply 29 applies an AC voltage between detection electrode 11 and counter electrode 16, thereby causing microorganisms contained in sample solution 31 to be moved toward detection unit 17 by dielectrophoresis. At the same time, oscillation circuit 22 applies an AC voltage between detection electrode 11 and counter electrode 23 to cause crystal piece 24 to oscillate. When microorganisms are captured in mold 15 of polymer layer 14, the mass of detection unit 17 changes, and the resonance frequency of crystal piece 24 changes. The frequency counter within controller 21 receives a signal from oscillation circuit 22 and measures a resonance frequency value. The state of capturing microorganisms is detected based on the change in the resonance frequency value.

By using QCM sensor 33 shown in FIG. 3, a polymer layer can be formed on detection electrode 11 in accordance with the step of roughening the surface of detection electrode 11 and the steps shown in FIG. 1. In these cases, the crystal oscillator formed by stacking detection electrode 11, crystal piece 24 and counter electrode 23 in this order is disposed at the bottom of cell 27, and a direct-current (DC) power supply is connected in place of AC power supply 29. When forming a polymer layer using QCM sensor 33, the progress status of formation of a polymer layer can be confirmed by monitoring the change in the resonance frequency of the crystal oscillator in accordance with formation of the polymer layer. When a plurality of types of microorganisms to be detected exist, their respective molds according to the present invention are formed separately and combined with one another, or molds corresponding to a plurality of microorganisms are simultaneously formed in a single mold, thereby allowing simultaneous detection of the plurality of types of microorganisms.

According to the sensor of the present invention, bacteria can also be detected in a few minutes to several dozen minutes, in which case bacteria can be detected much more quickly than in the case of the cultural method. Furthermore, since bacteria can be detected without using for example a staining reagent required for fluorescent staining and an ATP extracting reagent required for measuring the number of bacteria by the ATP, the sensor of the present invention can be readily automated or installed in devices such as a water filter, a water server or an automatic ice maker. Furthermore, the sensor of the present invention can also be used in a water purification plant and a beverage/food factory as a tool for a bacteria test in the water quality inspection and the food inspection. Further specifically, bacteria within equipment such as a water storage tank and a piping channel can be automatically detected, the detection result can be informed to the user, and measures such as sterilization, cleaning and the like can be automatically taken. The sensor of the present invention can also be installed as a device in the piping line of clean water in a water purification plant to detect bacteria in the water to be supplied.

The polymer layer in the above-described sensor can be used not only for a component of the sensor but also for a microorganism capturing device, a microorganism shape-recognizing device and a microorganism tracking device each utilizing a feature of a mold having a three-dimensional structure complementary to the steric structure of a microorganism, and also for a catalyst carrier utilizing a feature of a porous body, and the like.

EXAMPLES

The present invention will be hereinafter described with reference to Examples. The following Examples merely illustrate the present invention, but do not limit the present invention.

In Examples described below, a polymer layer was produced using an electrochemistry measurement system (Mode1842B manufactured by ALS). In this case, a gold electrode (corresponding to electrode 11 that is one of electrodes in a crystal oscillator) was used for a detection electrode; Ag/AgCl (saturation KCl) was used for a reference electrode; and a Pt rod (having a diameter of 1 mm, a length of 4 cm and manufactured by Nilaco corporation) was used for a counter electrode (first counter electrode). In the following description, the electric potential is indicated as a value with respect to the electric potential of this reference electrode. Furthermore, a crystal oscillator having both surfaces each provided with a gold electrode (an electrode area of 0.196 cm$^2$, a fundamental oscillation frequency of 9 MHz, AT cut, a square shape, and manufactured by SEIKO EG & G CO., LTD.) was used.

Figure 4:
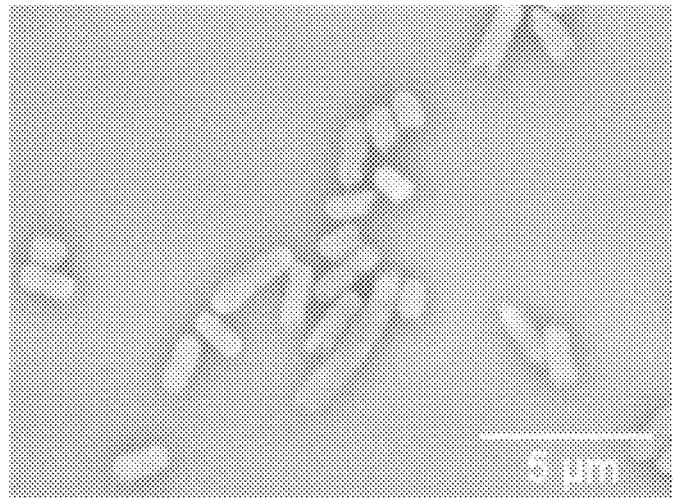
FIG. 4 is an electron microscope photograph of *Pseudomonas aeruginosa*.
Figure 5:
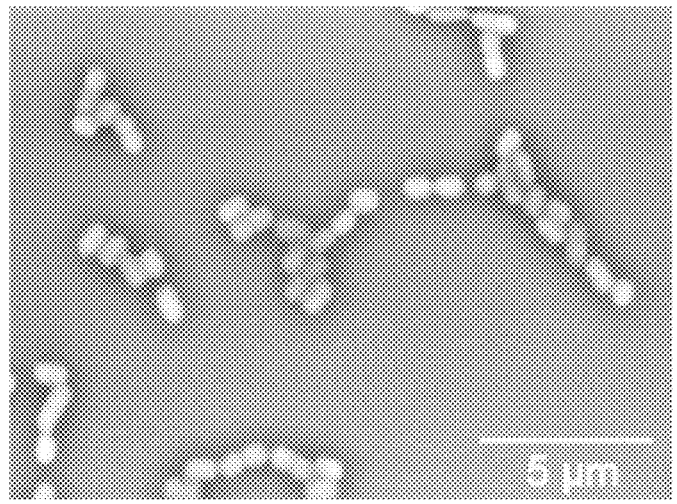
FIG. 5 is an electron microscope photograph of *Acinetobacter* calcoaceticus.

In Examples 1 and 4, *Pseudomonas aeruginosa* (zeta potential: −33.87 mV) was used as a microorganism to be detected. In Example 2, *Acinetobacter* calcoaceticus (zeta potential: −28.14 mV) was used. In Example 3, *Escherichia coli* were used. In Example 5, *Pseudomonas aeruginosa*, *Escherichia coli*, *Acinetobacter* calcoaceticus, and *Serratia marcescens* were used. FIGS. 4 and 5 show electron microscope photographs of *Pseudomonas aeruginosa* and *Acinetobacter* calcoaceticus, respectively.

It can be seen from the microscope photographs shown in FIGS. 4 and 5 that *Pseudomonas aeruginosa* has a shape of a rod, and *Acinetobacter* calcoaceticus has a shape closer to a sphere than that of *Pseudomonas aeruginosa*.

Example 1

<Production of Sensor>
(Surface-Roughening Step for Gold Electrode)
For the purpose of improving the adhesiveness to a peroxidized polypyrrole layer, a process of roughening the surface of the gold electrode of the multilayer body of the crystal oscillator was performed in accordance with the following procedure.

1. The surface of the gold electrode was etched for 30 seconds by a plasma etching equipment (SEDE/meiwa fosis).

2. The crystal oscillator was installed at the bottom of cell 27 of QCM sensor 33 as shown in FIG. 3. Then, 500 µL of a solution containing 30 nm of citric acid-protected gold nanoparticles (0.0574 wt %) was added into cell 27, and then allowed to stand at room temperature for 24 hours.

3. After the gold electrode was washed with pure water, 500 µL of a solution (growth liquid) obtained by mixing 9 mL of a hexadecyltrimethylammonium bromide solution (0.1 M), 250 µL it of chloroauric (III) acid tetrachloride (0.01 M), 50 µL of NaOH (0.1 M), and 50 µL of ascorbic acid (0.1 M) was added to cell 27 and allowed to remain at room temperature for 24 hours.

4. The solution within cell 27 was removed and the gold electrode was washed with ultrapure water.

(Production of Peroxidized Polypyrrole Layer Having Mold of Microorganism)
A peroxidized polypyrrole layer was produced on the gold electrode in accordance with the following procedure.

1. First, 0.1 M of a pyrrole aqueous solution containing *Pseudomonas aeruginosa* and a phosphate buffer solution (0.2 M, pH 2.56) was prepared to obtain a modified solution.

2. The modified solution was added into cell 27 of QCM Sensor 33 in which a gold electrode having undergone the surface-roughening process as described above was disposed, and the first counter electrode and the reference electrode were inserted into the modified solution.

3. Controlled-potential electrolysis (+0.975 V for 90 seconds) was carried out in the modified solution, thereby depositing polypyrrole on the gold electrode, to produce a polypyrrole layer (polymerization step). The resonance frequency of the crystal oscillator was also monitored in the polymerization step.

4. Lysozyme (10 mg/mL) was dripped on the produced polypyrrole layer, which was then shaken for 120 minutes, to which a 40% solution of a nonionic surface-active agent (trade name: triton) was subsequently added, and then shaken for 80 minutes (bacteriolysis step).

5. After the polypyrrole layer was washed with ultrapure water several times, 0.1 M of a NaOH solution was added into cell 27, to which +975 mV of a constant electrical potential was applied for 120 seconds to perform a peroxidation process, thereby obtaining a peroxidized polypyrrole layer (peroxidation step). The resonance frequency of the crystal oscillator was also monitored in the peroxidation step.

Figure 6:
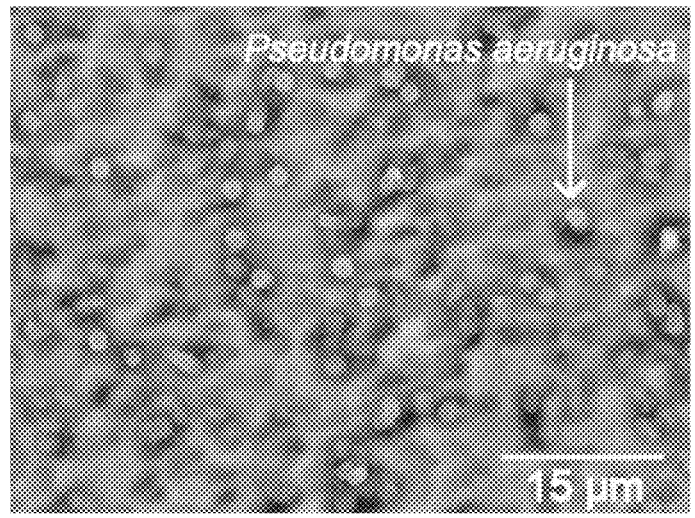
FIG. 6 is a diagram showing an electron microscope photograph of the surface of a polypyrrole layer after the polymerization step in Example 1.
Figure 7:
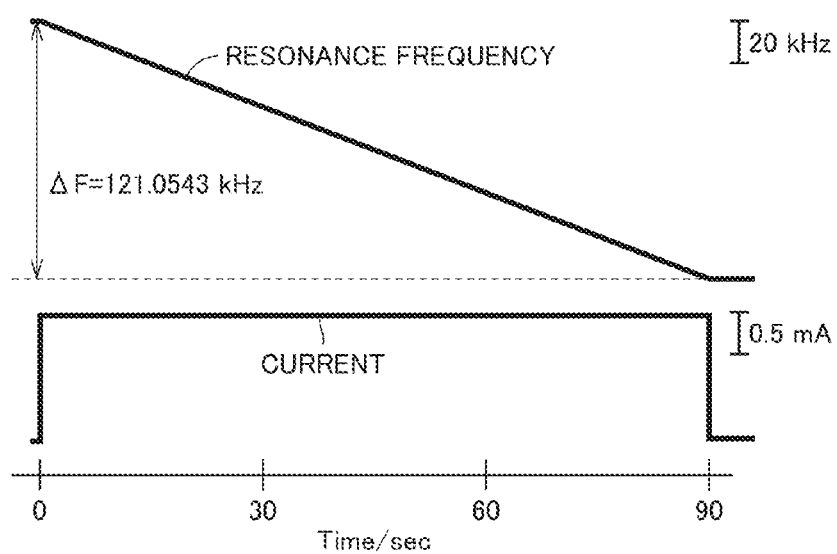
FIG. 7 is a graph showing the relation between the time and the current, and the relation between the time and the resonance frequency of the crystal oscillator in the polymerization step in Example 1.
Figure 8:
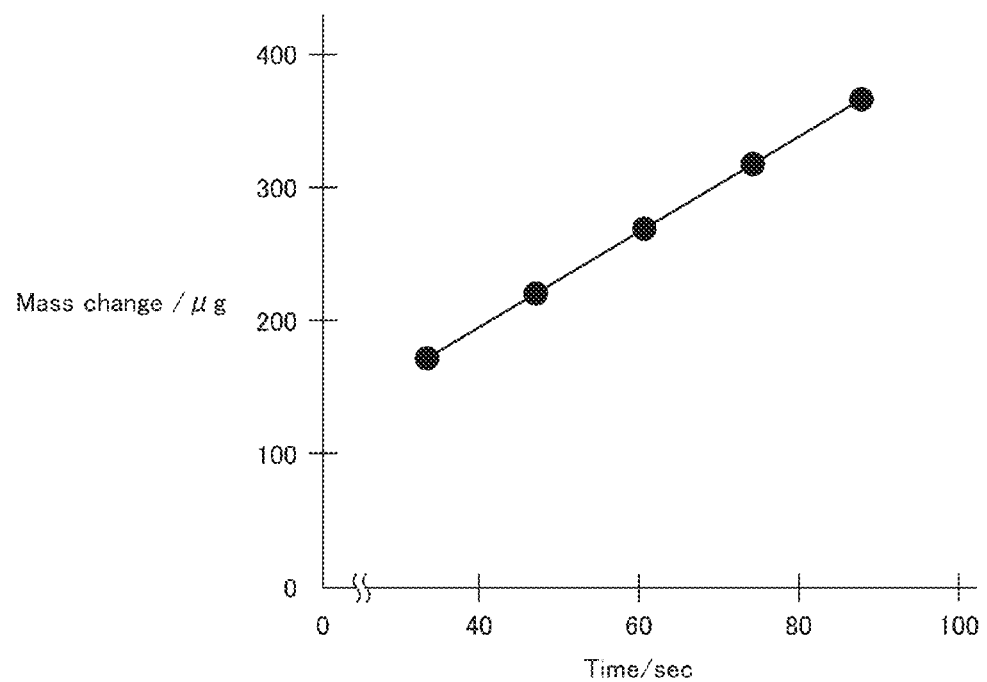
FIG. 8 is a graph showing the relation between the time and the mass change in Example 1.

(Results)
FIG. 6 shows an electron microscope photograph of the surface of the polypyrrole layer after the polymerization step. It was observed how *Pseudomonas aeruginosa* were captured in the surface of the polypyrrole layer. FIG. 7 is a graph showing the relation between the time and the current, and the relation between the time and the resonance frequency of the crystal oscillator in the polymerization step. The point of time at which the controlled potential electrolysis is started is set at 0 second. FIG. 8 is a graph showing the relation between the time and the mass change obtained by calculating the amount of mass change of the crystal oscillator based on the amount of change in the resonance frequency shown in FIG. 7. These graphs show that the mass of the surface of the crystal oscillator increased in proportion to the electrolysis time, and a sufficient mass change, that is, sufficient polymerization of the polypyrrole layer, was achieved in 90 seconds.

Figure 9:
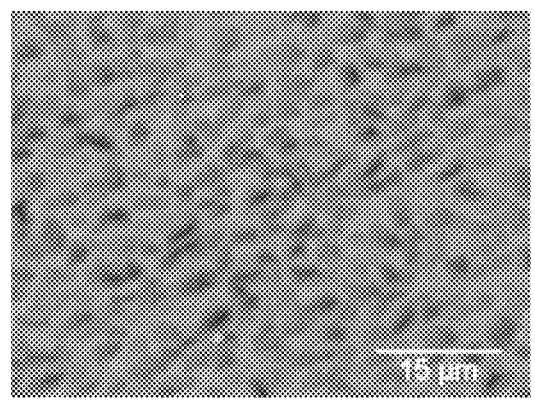
FIG. 9 is an electron microscope photograph of the surface of the peroxidized polypyrrole layer after the bacteriolysis step and the peroxidation step in Example 1.
Figure 10:
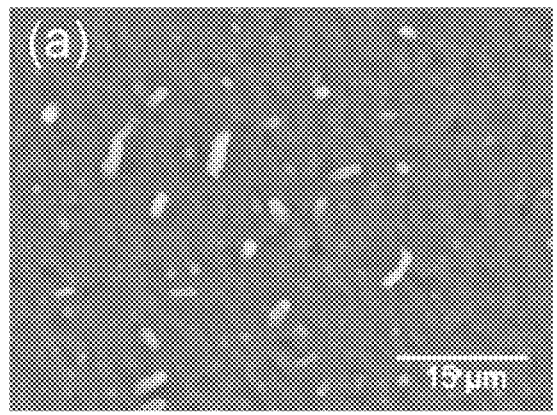
FIG. 10 is an electron microscope photograph of the surface of the peroxidized polypyrrole layer after the bacteriolysis step and the peroxidation step in the case where the bacteriolysis conditions are changed from those in Example 1.
Figure 10:
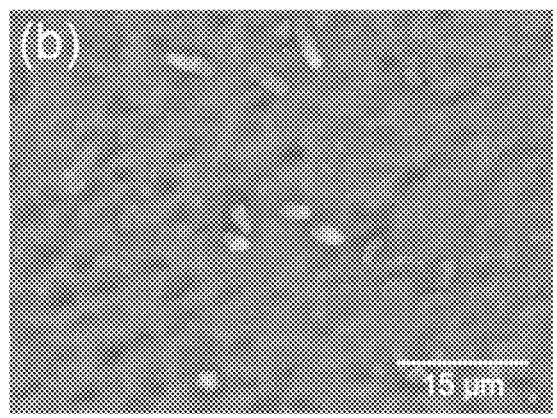
Figure 10:
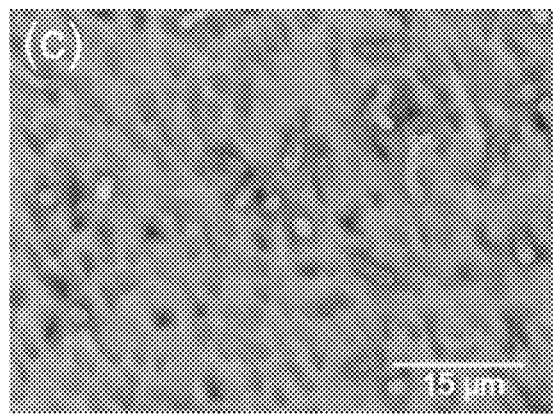

FIG. 9 shows an electron microscope photograph of the surface of the peroxidized polypyrrole layer after the bacteriolysis step and the peroxidation step. *Pseudomonas aeruginosa* were not observed on the surface of the peroxidized polypyrrole layer. Accordingly, it is found that *Pseudomonas aeruginosa* were released from the surface of the peroxidized polypyrrole layer. FIG. 10 shows an electron microscope photograph of the surface of the peroxidized polypyrrole layer produced on the conditions different from those of the above-described Example 1 in the shaking time period after dripping lysozyme and the shaking time period after adding a nonionic surface-active agent in the bacteriolysis step. FIG. 10(*a*) shows an electron microscope photograph in the case where the shaking time period after dripping lysozyme was set at 30 minutes and the shaking time period after adding a nonionic surface-active agent was set at 20 minutes. FIG. 10(*b*) shows an electron microscope photograph in the case where the shaking time period after dripping lysozyme was set at 60 minutes and the shaking time period after adding a nonionic surface-active agent was set at 40 minutes. FIG. 10(*c*) shows an electron microscope photograph in the case where the shaking time period after dripping lysozyme was set at 90 minutes and the shaking time period after adding a nonionic surface-active agent was set at 60 minutes. It can be seen from FIGS. 10(*a*) to 10(*c*) that *Pseudomonas aeruginosa* are not sufficiently released under the above-described conditions, and therefore, it is suitable to employ the condition for the bacteriolysis step in Example 1.

Figure 11:
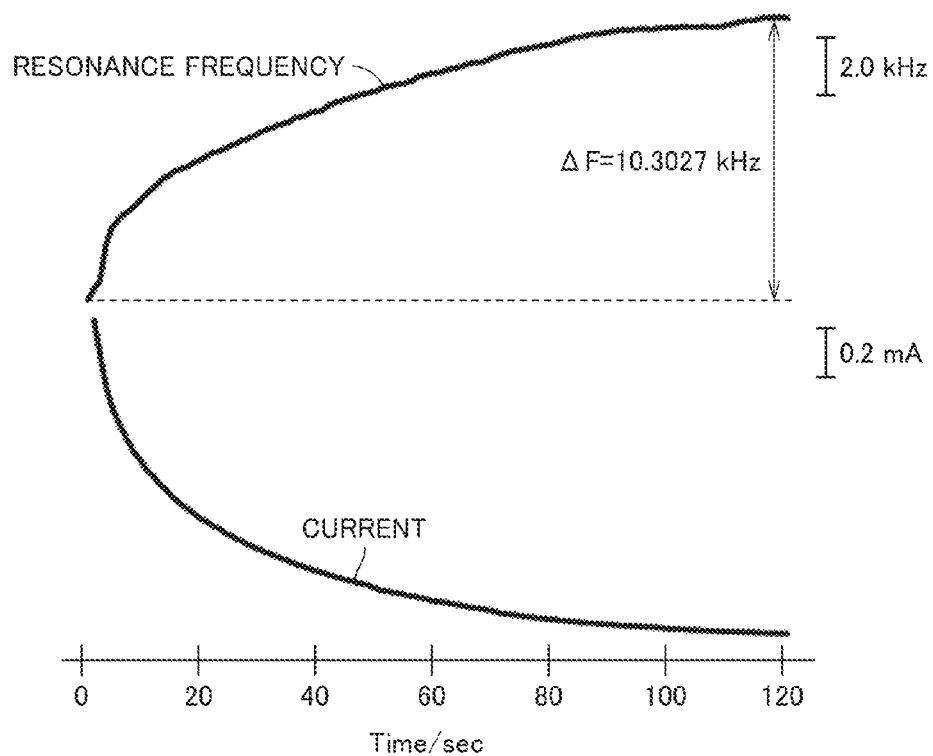
FIG. 11 is a graph showing the relation between the time and the current, and the relation between the time and the resonance frequency of the crystal oscillator in the peroxidation step in Example 1.

FIG. 11 is a graph showing the relation between the time and the current, and the relation between the time and the resonance frequency of the crystal oscillator in the peroxidation step. The time at which a constant electrical potential is applied in the peroxidation step is set at 0 second. It is found that the current value decreases with time, and the peroxidation process progresses. It is also found that the resonance frequency increases and the mass of the electrode surface decreases. It is understood that this is caused by releasing *Pseudomonas aeruginosa*.

\<Detection of Microorganism\>

(Detection Experiment)

Microorganisms were detected using a QCM sensor having a crystal oscillator provided at the bottom of a cell. This crystal oscillator had a surface on which a peroxidized polypyrrole layer produced as described above and having a *Pseudomonas aeruginosa* mold was formed. A sample solution containing microorganisms was added into the cell. Then, an AC voltage was applied between a gold electrode and the first counter electrode, to cause the microorganisms to be concentrated on the surface of the peroxidized polypyrrole layer by dielectrophoresis. A waveform generator (7075; manufactured by HIOKI E.E. CORPORATION) was used to generate an AC voltage (waveform: a sinusoidal wave, voltage: 2 Vpp, and frequency: 10 MHz). An amplifier (HAS4101; manufactured by NF Corporation) was used to amplify the voltage 10 times and apply this voltage at 20 Vpp. Also, the resonance frequency of the crystal oscillator during voltage application was monitored.

(Results)

Figure 12:
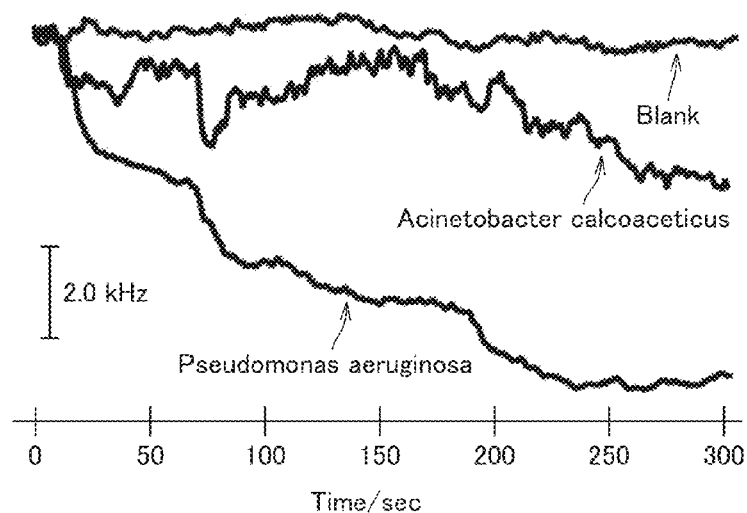
FIG. 12 is a graph showing the relation between the time of applying an AC voltage and the resonance frequency of the crystal oscillator during detection of microorganisms using a sensor in Example 1.

FIG. 12 is a graph showing the relation between the time of applying an AC voltage and the resonance frequency of the crystal oscillator. It has been found from the results shown in FIG. 12 that the resonance frequency greatly decreased in the detection experiment in which a sample solution containing *Pseudomonas aeruginosa* was added. The decrease in resonance frequency means that the mass of the surface of the crystal oscillator has increased. It is considered that dielectrophoretic force acted on *Pseudomonas aeruginosa*, which was then captured in the mold of the peroxidized polypyrrole layer, with the result that the mass of the surface of the crystal oscillator has increased. On the other hand, in the case of *Acinetobacter* calcoaceticus having a shape different from the mold, there has been almost no change in the mass as in the case of a blank. Therefore, it is considered that *Acinetobacter* calcoaceticus having a shape different from the mold is not so readily captured in the peroxidized polypyrrole layer as compared with *Pseudomonas aeruginosa*. Thus, it can be determined that the sensor recognizes the type of bacteria with high accuracy.

Example 2

\<Production of Sensor\>

The step of roughening the surface of the gold electrode, the polymerization step, the bacteriolysis step and the peroxidation step were performed as in Example 1 except that *Acinetobacter* calcoaceticus was used in place of *Pseudomonas aeruginosa* in Example 1.

(Results)

Figure 13:
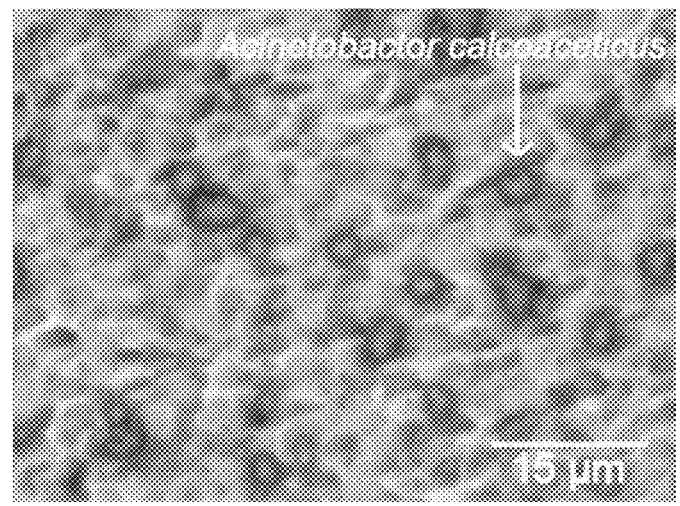
FIG. 13 is a diagram showing an electron microscope photograph of the surface of the polypyrrole layer after the polymerization step in Example 2.
Figure 14:
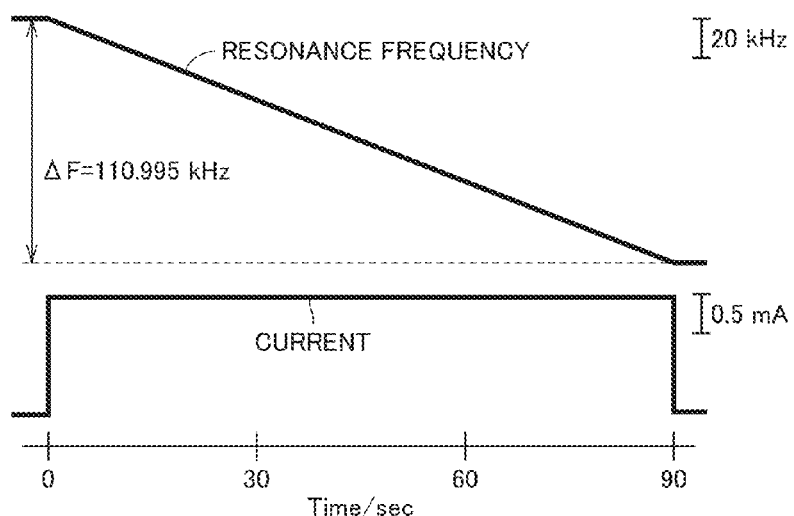
FIG. 14 is a graph showing the relation between the time and the current, and the relation between the time and the resonance frequency of the crystal oscillator in the polymerization step in Example 2.

FIG. 13 shows an electron microscope photograph of the surface of the polypyrrole layer after the polymerization step. It was observed how *Acinetobacter* calcoaceticus was captured in the surface of the polypyrrole layer. FIG. 14 is a graph showing the relation between the time and the current, and the relation between the time and the resonance frequency of the crystal oscillator in the polymerization step. The time at which the controlled potential electrolysis is started is set at 0 second. This graph shows that the mass of the surface of the crystal oscillator increased in proportion to the electrolysis time.

Figure 15:
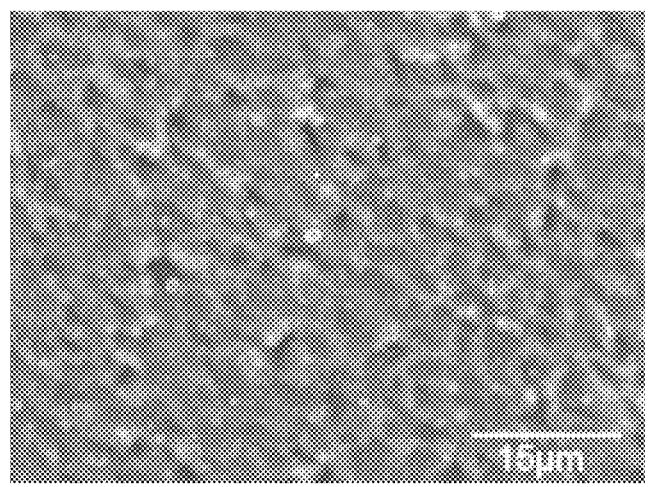
FIG. 15 is an electron microscope photograph of the surface of the peroxidized polypyrrole layer after the bacteriolysis step and the peroxidation step in Example 2.

FIG. 15 is an electron microscope photograph of the surface of the peroxidized polypyrrole layer after the bacteriolysis step and the peroxidation step. No *Acinetobacter* calcoaceticus was observed on the surface of the peroxidized polypyrrole layer. Accordingly, it is found that *Acinetobacter* calcoaceticus was released from the surface of the peroxidized polypyrrole layer.

Figure 16:
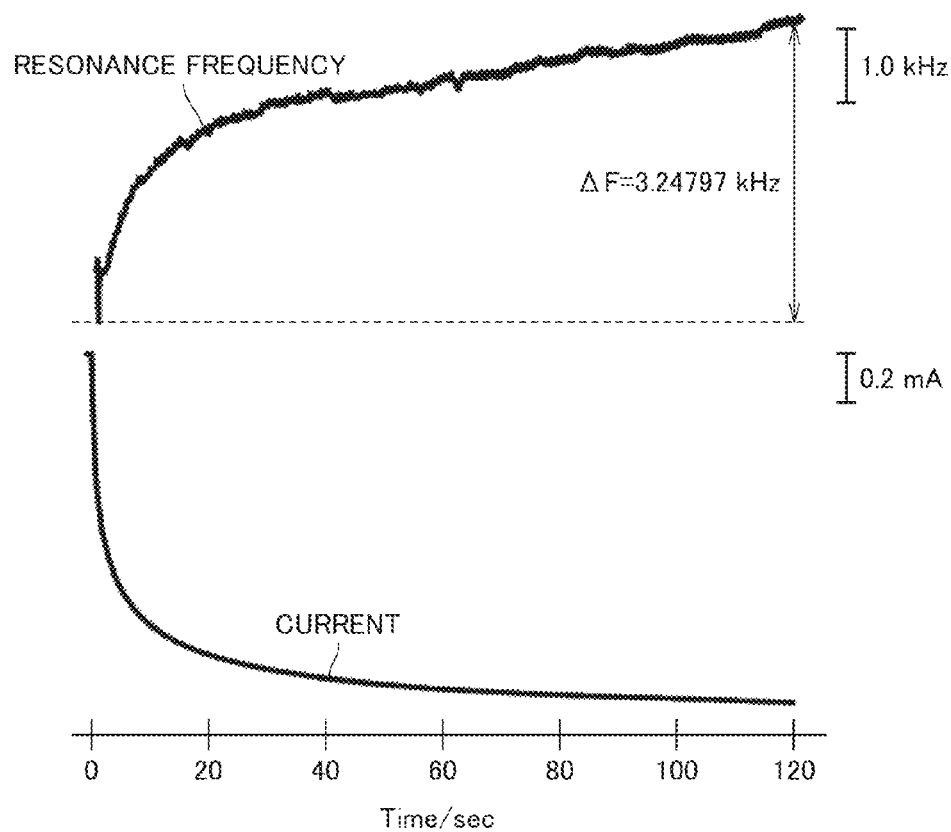
FIG. 16 is a graph showing the relation between the time and the current, and the relation between the time and the resonance frequency of the crystal oscillator in the peroxidation step in Example 2.

FIG. 16 is a graph showing the relation between the time and the current, and the relation between the time and the resonance frequency of the crystal oscillator in the peroxidation step. The time at which a constant electrical potential is applied in the peroxidation step is set at 0 second. It is found that the current value decreases with time, and the peroxidation step progresses. It is also found that the resonance frequency increases and the mass of the electrode surface decreases. It is understood that this is caused by releasing *Acinetobacter* calcoaceticus.

\<Detection of Microorganism\>

(Detection Experiment)

Microorganisms were detected using a QCM sensor having a crystal oscillator provided at the bottom of a cell. This crystal oscillator had a surface on which a peroxidized polypyrrole layer produced as described above and having an *Acinetobacter* calcoaceticus mold was formed. The same experimental conditions as those in Example 1 were used.

(Results)

Figure 17:
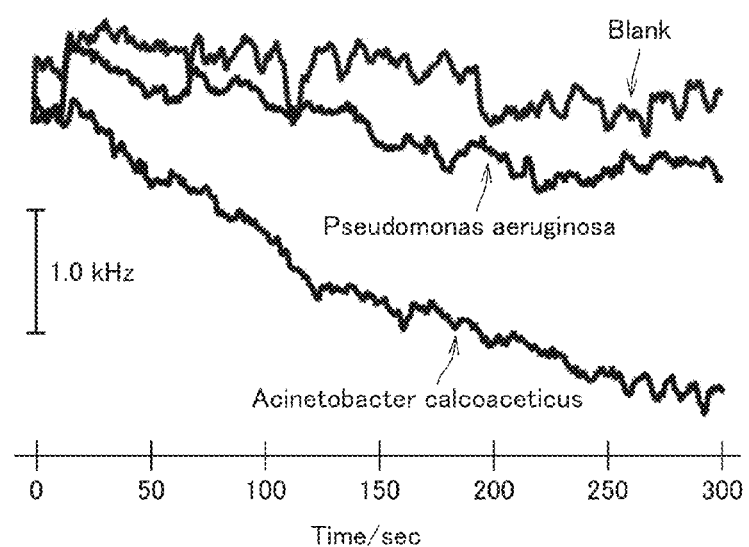
FIG. 17 is a graph showing the relation between the time of applying an AC voltage and the resonance frequency of the crystal oscillator during detection of microorganisms using a sensor in Example 2.

FIG. 17 is a graph showing the relation between the time of applying an AC voltage and the resonance frequency of the crystal oscillator. It has been found from the results shown in FIG. 17 that the resonance frequency greatly decreased in the detection experiment in which the sample solution containing *Acinetobacter* calcoaceticus was added. The decrease in resonance frequency means that the mass of the surface of the crystal oscillator has increased. Thus, it is considered that dielectrophoretic force acted on *Acinetobacter* calcoaceticus, which was then captured in the mold of the peroxidized polypyrrole layer, with the result that the mass of the surface of the crystal oscillator has increased. On the other hand, in the case of *Pseudomonas aeruginosa* having a shape different from the mold, there has been almost no change in the mass as in the case of a blank. Therefore, it is considered that *Pseudomonas aeruginosa* having a shape different from the mold is not so readily captured in the peroxidized polypyrrole layer as compared with *Acinetobacter* calcoaceticus. Thus, it can be determined that the sensor recognizes the type of bacteria with high accuracy.

Example 3

\<Production of Sensor\>

The step of roughening the surface of the gold electrode, the polymerization step, the bacteriolysis step and the peroxidation step were performed as in Example 1 except that *Escherichia coli* were used in place of *Pseudomonas aeruginosa* in Example 1.

\<Detection of Microorganism\>

(Detection Experiment)

Microorganisms were detected using a QCM sensor having a crystal oscillator provided at the bottom of a cell. This crystal oscillator had a surface on which a peroxidized polypyrrole layer produced as described above and having an *Escherichia coli* mold was formed. As measurement samples, solutions of *Pseudomonas aeruginosa, Escherichia coli* and *Acinetobacter* calcoaceticus, respectively, were used.

(Results)

Figure 18:
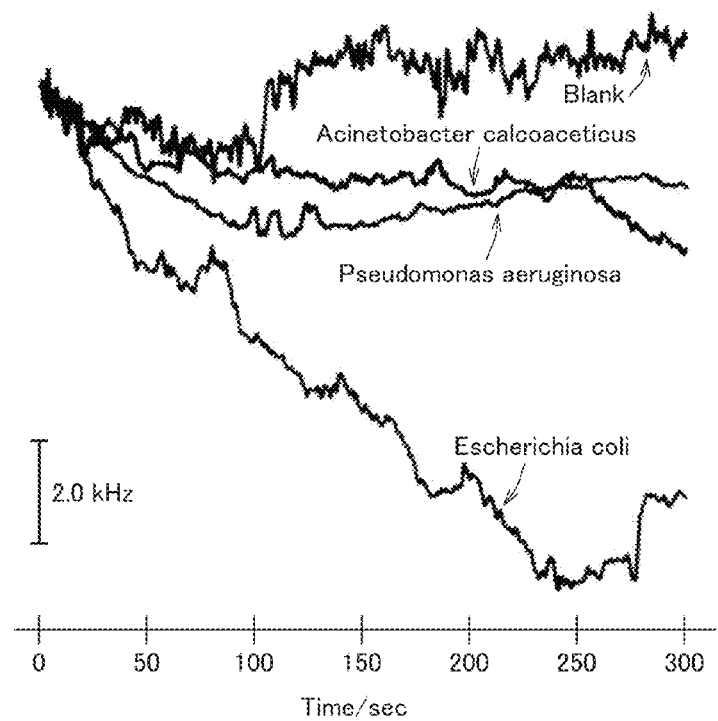
FIG. 18 is a graph showing the relation between the time of applying an AC voltage and the resonance frequency of the crystal oscillator during detection of microorganisms using a sensor in Example 3.

FIG. 18 is a graph showing the relation between the time of applying an AC voltage and the resonance frequency of the crystal oscillator. It has been found from the results shown in FIG. 18 that the resonance frequency greatly decreased in the detection experiment in which the sample solution containing *Escherichia coli* was added. The decrease in resonance frequency means that the mass of the surface of the crystal oscillator has increased. Thus, it is considered that dielectrophoretic force acted on Escherichia coli, which was then captured in the mold of the peroxidized polypyrrole layer, with the result that the mass of the surface of the crystal oscillator has increased. On the other hand, in the cases of Pseudomonas aeruginosa and Acinetobacter calcoaceticus each having a shape different from the mold, there has been almost no change in the mass as in the case of a blank. Therefore, it is considered that Pseudomonas aeruginosa and Acinetobacter calcoaceticus each having a shape different from the mold is not so readily captured in the peroxidized polypyrrole layer as compared with Escherichia coli. Thus, it can be determined that the sensor recognizes the type of bacteria with high accuracy.

Example 4

<Production of Sensor>

Using Pseudomonas aeruginosa, the step of roughening the surface of the gold electrode, the polymerization step, the bacteriolysis step and the peroxidation step were performed as in Example 1.

<Detection of Microorganism>

(Detection Experiment)

Microorganisms were detected using a QCM sensor having a crystal oscillator provided at the bottom of a cell. This crystal oscillator had a surface on which a peroxidized polypyrrole layer produced as described above and having a Pseudomonas aeruginosa mold was formed. As measurement samples, two types of solutions were used, including a solution (a) obtained by mixing solutions of Pseudomonas aeruginosa, Escherichia coli, Acinetobacter calcoaceticus, and serratia bacteria; and a solution (b) obtained by mixing solutions of Escherichia coli, Acinetobacter calcoaceticus and serratia bacteria.

(Results)

Figure 19:
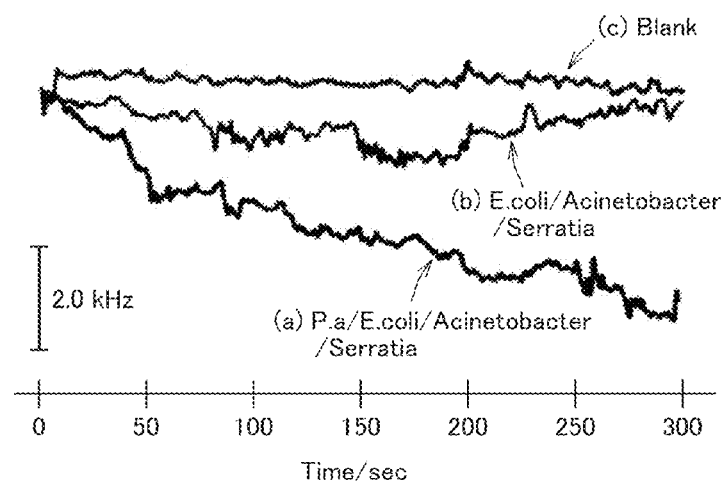
FIG. 19 is a graph showing the relation between the time of applying an AC voltage and the resonance frequency of the crystal oscillator during detection of microorganisms using a sensor in Example 4.
Figure 20:
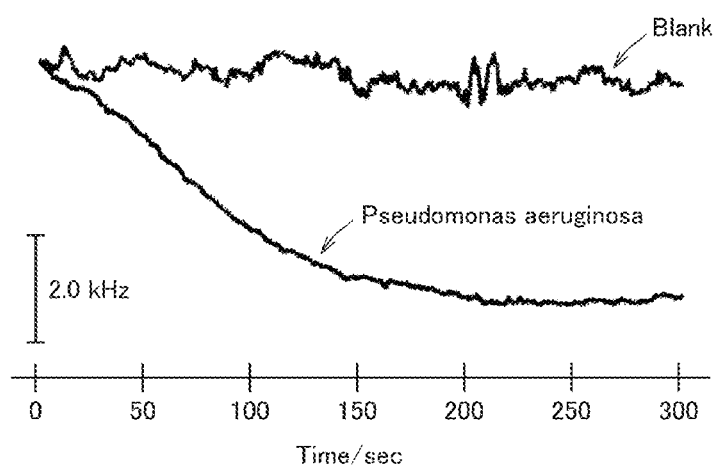
FIG. 20 is a graph showing the relation between the time of applying an AC voltage and the resonance frequency of the crystal oscillator in the detection experiment in which a sample solution containing *Pseudomonas aeruginosa* is added to a sensor in Example 5.
Figure 21:
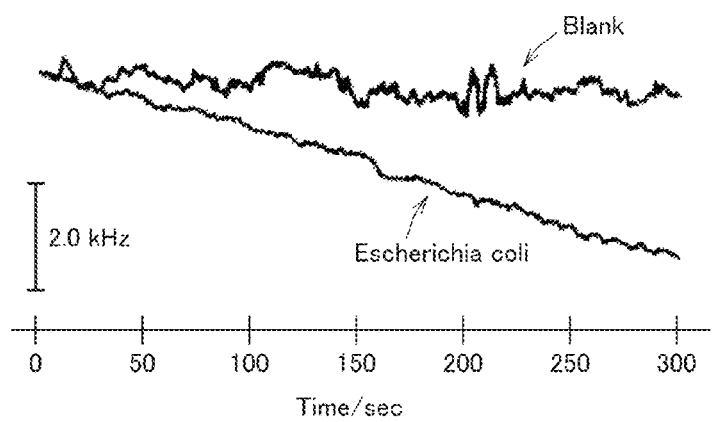
FIG. 21 is a graph showing the relation between the time of applying an AC voltage and the resonance frequency of the crystal oscillator in the detection experiment in which a sample solution containing *Escherichia coli* is added to the sensor in Example 5.
Figure 22:
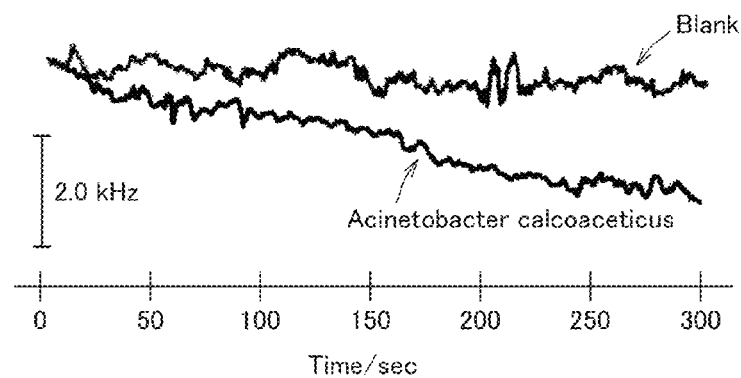
FIG. 22 is a graph showing the relation between the time of applying an AC voltage and the resonance frequency of the crystal oscillator in the detection experiment in which a sample solution containing *Acinetobacter* calcoaceticus is added to the sensor in Example 5.
Figure 23:
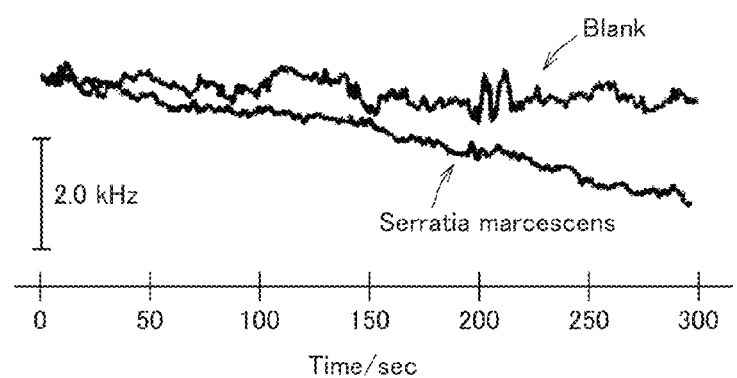
FIG. 23 is a graph showing the relation between the time of applying an AC voltage and the resonance frequency of the crystal oscillator in the detection experiment in which a sample solution containing *serratia* bacteria is added to the sensor in Example 5.

FIG. 19 is a graph showing the relation between the time of applying an AC voltage and the resonance frequency of the crystal oscillator. It has been found from the results shown in FIG. 19 that the resonance frequency greatly decreased in the detection experiment in which the sample solution containing Pseudomonas aeruginosa was added. The decrease in resonance frequency means that the mass of the surface of the crystal oscillator has increased. Thus, it is considered that dielectrophoretic force acted on Pseudomonas aeruginosa, which was then captured in the mold of the peroxidized polypyrrole layer, with the result that the mass of the surface of the crystal oscillator has increased. On the other hand, in the case of Escherichia coli, Acinetobacter calcoaceticus and Serratia bacteria each having a shape different from the mold, there has been almost no change in the mass as in the case of a blank (c). Therefore, it is considered that Escherichia coli, Acinetobacter calcoaceticus and Serratia bacteria each having a shape different from the mold is not so readily captured in the peroxidized polypyrrole layer as compared with Pseudomonas aeruginosa. Thus, it can be determined that the sensor recognizes the type of bacteria with high accuracy.

Example 5

<Production of Sensor>

Using a modified solution containing all of Pseudomonas aeruginosa, Escherichia coli, Acinetobacter calcoaceticus, and serratia bacteria, the step of roughening the surface of the gold electrode, the polymerization step, the bacteriolysis step and the peroxidation step were performed as in Example 1.

<Detection of Microorganism>

(Detection Experiment)

Microorganisms were detected using a QCM sensor having a crystal oscillator provided at the bottom of a cell. This crystal oscillator had a surface on which a peroxidized polypyrrole layer produced as described above and having molds including four types of microorganisms was formed. As measurement samples, four types of solutions containing Pseudomonas aeruginosa, Escherichia coli, Acinetobacter calcoaceticus, and serratia bacteria, respectively, were used.

(Results)

FIGS. 20 to 23 each are a graph showing the relation between the time of applying an AC voltage and the resonance frequency of the crystal oscillator. FIGS. 20 to 23 show the results in the detection experiments in which sample solutions containing Pseudomonas aeruginosa, Escherichia coli, Acinetobacter calcoaceticus, and serratia bacteria, respectively, were added. It has been found that the resonance frequency greatly decreased when any of the sample solutions was added. Accordingly, it can be determined that a plurality of types of microorganisms are detected by the sensor having molds of a plurality of types of microorganisms.

Reference Signs List 11 detection electrode, 12 solution, 13 microorganism, 14 polymer layer, 15 mold, 16 counter electrode (first counter electrode), 17 detection unit, 21 controller, 22 oscillation circuit, 23 counter electrode (second counter electrode), 24 crystal piece, 27 cell, 29 AC power supply, 30 reference electrode, 31 sample solution, 32 crystal oscillator, 33 QCM sensor.

The invention claimed is:

1. A sensor for detecting a microorganism based on a state of capturing said microorganism in a mold, said sensor comprising
   (A) a detection unit including a detection electrode and a polymer layer that is disposed on a roughened surface of said detection electrode and includes a mold having a three-dimensional structure complementary to a steric structure of a microorganism to be detected, wherein said microorganism has entire electric charge or electric charge on a surface thereof that is excessively negatively charged, and wherein said polymer layer is made of polypyrrole, polvaniline, polythiophene, or derivatives thereof, said polymer layer being formed by a manufacturing method including: a polymerization step of polymerizing a monomer in presence of the microorganism to be detected, to form said polymer layer having captured said microorganism on said detection electrode; a destruction step of partially destroying the microorganism captured in said polymer layer; and a peroxidation step of peroxidizing said polymer layer to release said microorganism from said polymer layer, thereby imparting to said polymer layer a three-dimensional structure complementary to a steric structure of said microorganism, and
   (B) a counter electrode, wherein said sensor is adapted to supply alternating-current voltage between said detection electrode and said counter electrode in a state where said detection unit and said counter electrode are in contact with a sample solution, to direct said microorganism in said sample solution toward said detection unit by dielectrophoresis.

2. The sensor according to claim 1, wherein said polymer layer is made of polypyrrole or derivatives thereof.

3. The sensor according to claim 1, wherein said polymer layer is made of polyaniline, polythiophene, or derivatives thereof.

4. The sensor according to claim 2, further comprising a crystal oscillator having said detection electrode of said detection unit as one of electrodes, wherein
said sensor measures a change in a mass of said polymer layer based on a change in a resonance frequency of said crystal oscillator to detect the state of capturing said microorganism.

5. The sensor according claim 2, wherein said microorganism is a bacterium, and a bacteriolysis process is performed in said destruction step.

6. The sensor according to claim 5, wherein said bacterium is *Pseudomonas aeruginosa*, *Acinetobacter* calcoaceticus, or *Escherichia coli*.

7. A method of manufacturing a sensor of claim 1, comprising:
a polymerization step of polymerizing a monomer in presence of the microorganism to be detected, to form said polymer layer having captured said microorganism on said detection electrode, wherein said microorganism has entire electric charge or electric charge on a surface thereof that is excessively negatively charged, and wherein said polymer layer is made of polypyrrole, polyaniline, polythiophene, derivatives thereof,;
a destruction step of partially destroying the microorganism captured in said polymer layer; and
a step of peroxidizing said polymer layer to release said microorganism from said polymer layer.

8. The method of manufacturing a sensor according to claim 7, wherein
said sensor further includes a counter electrode, and
said polymerization step includes a step of applying a voltage between said detection electrode and said counter electrode that are in contact with a solution of said monomer, to electropolymerize said monomer.

9. The method of manufacturing a sensor according to claim 7, wherein said peroxidizing step includes a step of applying a voltage between said detection electrode and said counter electrode that are in contact with a solution within a range from neutral to alkaline, to peroxidize said polymer layer.

10. The method of manufacturing a sensor according to claim 7, comprising a surface-roughening step of roughening a surface of said detection electrode on which said polymer layer is formed.

11. A polymer layer including a mold having a three-dimensional structure complementary to a steric structure of a microorganism,
said polymer layer being formed by a manufacturing method including: a polymerization step of polymerizing a monomer in presence of said microorganism to form said polymer layer, wherein said polymer layer is made of polypyrrole, polyaniline, polythiophene, or derivatives thereof; a destruction step of partially destroying the microorganism captured in said polymer layer; and a peroxidation step of releasing said microorganism from said polymer layer.

12. The polymer layer accordingly to claim 11, wherein said polymer layer is made of polypyrrole or derivatives thereof

* * * * *